United States Patent
Wada et al.

(10) Patent No.: US 6,593,358 B1
(45) Date of Patent: Jul. 15, 2003

(54) THIENYL-PYRAZOLES AND THEIR USE FOR CONTROLLING PESTS

(75) Inventors: Katsuaki Wada, Tochigi (JP); Takuya Gomibuchi, Ibaraki (JP); Shinichi Narabu, Ibaraki (JP); Yuichi Otsu, Tochigi (JP); Katsuhiko Shibuya, Tochigi (JP); Takahisa Abe, Hokkaido (JP)

(73) Assignee: Nihon Bayer Agrochem K.K., Tokyo (JP)

( * ) Notice: Subject to any disclaimer, the term of this patent is extended or adjusted under 35 U.S.C. 154(b) by 0 days.

(21) Appl. No.: 10/030,930

(22) PCT Filed: Jul. 3, 2000

(86) PCT No.: PCT/IB00/00891

§ 371 (c)(1),
(2), (4) Date: Jan. 11, 2002

(87) PCT Pub. No.: WO01/05787

PCT Pub. Date: Jul. 3, 2000

(30) Foreign Application Priority Data

Jul. 15, 1999 (JP) .......................... 11-201444

(51) Int. Cl.$^7$ ........................ A01N 43/56; C07D 409/04
(52) U.S. Cl. ................................... 514/407; 548/365.7
(58) Field of Search ........................ 548/365.7; 514/407

(56) References Cited

U.S. PATENT DOCUMENTS

| | | |
|---|---|---|
| 2,630,437 A | 3/1953 | Homeyer |
| 3,700,416 A | 10/1972 | Lucid |
| 3,991,073 A | 11/1976 | Mulder et al. |
| 4,645,777 A | 2/1987 | Burkart et al. |
| 4,791,124 A | 12/1988 | Lutomski et al. |
| 4,908,357 A | 3/1990 | Lutomski |
| 4,939,165 A | 7/1990 | Burkart et al. |

FOREIGN PATENT DOCUMENTS

| | | |
|---|---|---|
| EP | 0 846 686 | 6/1998 |
| FR | 2 699 919 | 7/1994 |
| JP | 8-12617 | 1/1996 |

OTHER PUBLICATIONS

Lopez et al, chem Abstracts, vol. 119, No. 180, 297, 1993.*
Gupta et al., "Synthesis, anthelmintic and antiacetylcholinesterase activity of newer furan derivatives" Chemical Abstracts +Indexes, US, American Chemical Society. Columbus, vol. 110, No. 17, Apr. 24, 1989, XP002134796 ISSN: 0009–2258 abstract.
Database Chemabs 'Online!Chemical Abstracts Service, Columbus, Ohio, US: Lopez, Concepcion et al: "A carbon–13 NMR spectroscopic study of the structure of N–H pyrazoles and indazoles"retrieved from STN Database accession no. 119:180297 XP002154782 compounds with RN= 128228–96–6; 150433–23–1 & Can. J. Chem. (1993), 71(5), 678–84.

Database Chemabs 'Online!Chemical Abstracts Service, Columbus, Ohio, US; Nakhmanovich, A.S. et al: "Synthesis and reactions of alkylacetylenic alcohols and ketones of the thiophene series" retrieved from STN Database accession no. 74:87722 XP001154783 cited in the application compounds with RN = 31618–80–1; 31618–81–2; 31618–82–3 & Kim. Geterotsikl. Soedin. (1970), (7), 894–7.
Database Chemabs 'Online!Chemical Abstracts Service, Columbus, Ohio, US: Ishikawa, Hiromichi et al "Preparation of triazoles and their use as herbicides" retrieved form STN Database accession no. 120:99438 XP002154784 compound with RN= 31618–80–1 & JP 05 255316 A (Hokko Chem Ind Co, Japan) Oct. 5, 1993.
Tetrahedron, vol. 26, (month unavailable) 1970, pp. 4691–4696, Z. Yoshida and H. Ogoshi, "Cyclopropyl Conjugation with Chelate Ring of β–Diketones".
Zh. Org. Khim., 15, (1), (month unavailable) 1979, pp. 67–63.
J. Parkt. Chem., vol. 315, No 1, (lmonth Unavailable) 1973, pp. 31–38, Von E. Uhleman adn F. Dietze, "Säurestäke unterschiedlich substituerter Pivaloylacylmethane".

\* cited by examiner

Primary Examiner—Robert W. Ramsuer
(74) Attorney, Agent, or Firm—Richard E. L. Henderson; Raymond J. Harmuth

(57) ABSTRACT

The present invention relates to compounds of the formulae (Ia) and (Ib)

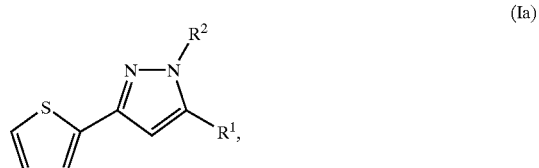

(Ia)

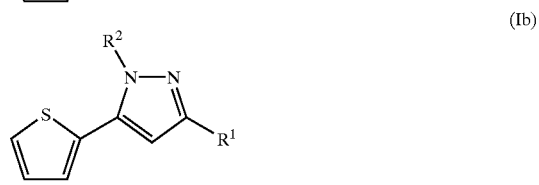

(Ib)

wherein $R^1$ represents $C_{1-10}$ alkyl which may be unsubstituted or substituted with halogen, or represents $C_{2-4}$ alkoxyalkyl, $C_{2-4}$ hydroxyalkyl, $C_{3-6}$ cycloalkyl, hydroxy, $C_{1-9}$ alkoxy which may be unsubstituted or substituted with halogen, or represents $C_{3-6}$ cycloalkoxy, $C_{2-4}$ alkoxyalkoxy or $C_{3-4}$ alkynyloxy, and $R^2$ represents hydrogen, $C_{1-4}$ alkoxycarbonyl, $C_{1-3}$ alkylcarbonyl or $C_{2-4}$ alkoxyalkyl, to processes for their preparation and to their use for controlling animal pests.

6 Claims, No Drawings

THIENYL-PYRAZOLES AND THEIR USE FOR CONTROLLING PESTS

The present invention relates to thienyl-pyrazoles and their use for controlling animals pests.

Khim. Geterotsikl. Soedin., 1970 (7), 894–897 describes 3-(2-thienyl)-5-methylpyrazole, 3-(2-thienyl)-5-n-butylpyrazole and 3-(2-thienyl)-5-n-pentylpyrazole; U.S. Pat. No. 2,630,437 describes 3-(2-thienyl)-5-hydroxypyrazole; Zh. Org. Khim., 15 (1), 57–63, 1979 describes 3-(2-thienyl)-5-phenyl-1H-pyrazole; J. Electron Spectrosc. Relat. Phenom. 31 (4), 317–21, 1983 describes 3-(2-thienyl)-5-(4-methoxyphenyl)-1H-pyrazole. None of these publications, however, describes or suggests that the above-mentioned pyrazole derivatives have nematicidal activity.

Further, WO 87/06429 discloses certain kinds of insecticidal oxazole or thiazole derivatives and WO 86/05949 discloses certain kinds of insecticidal bithienyl derivatives.

It has now been found that a group of thienyl-pyrazoles of the following formulae (Ia) and (Ib) can be used for controlling animal pests. They exhibit a particularly high nematicidal activity.

Therefore, the present invention provides compounds of the formulae (Ia) and (Ib)

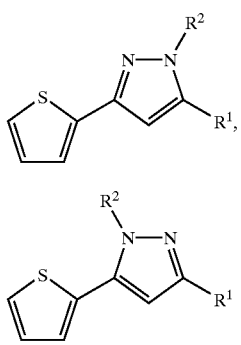

wherein
$R^1$ represents $C_{1-10}$ alkyl which may be unsubstituted or substituted with halogen, or represents hydroxy, $C_{2-4}$ alkoxyalkyl, $C_{2-4}$ hydroxyalkyl, $C_{3-6}$ cycloalkyl, hydroxy, $C_{1-9}$ alkoxy which may be unsubstituted or substituted with halogen, or represents $C_{3-6}$ cycloalkoxy, $C_{2-4}$ alkoxyalkoxy or $C_{3-4}$ alkinyloxy, $R^2$ represents hydrogen, $C_{1-4}$ alkoxycarbonyl, $C_{1-3}$ alkylcarbonyl or $C_{2-4}$ alkoxyalkyl and their use for controlling animal pests.

In case $R^2$ represents hydrogen, the formula (Ia) and the formula (Ib) are tautomers.

In case $R^2$ represents another group than hydrogen, the formula (Ia) and the formula (Ib) are regio isomers.

Each of the isomers of the above-mentioned formulae (Ia) and (Ib) can exist and can be used according to the present invention in a substantially pure form or as a mixture of different ratios.

The compounds of the formulae (Ia) and (Ib), excluding the cases in which $R^1$ represents methyl, n-butyl, n-pentyl or hydroxy and $R^2$ represents hydrogen, are novel compounds which were not described in the literature up to the present.

The thienyl-pyrazoles of the formula (Ia) and formula (Ib), wherein $R^1$ represents methyl, n-butyl, n-pentyl or hydroxy and $R^2$ represents a hydrogen, are described in Khim. Geterotsikl. Soedin., 1970 (7), 894–897 and U.S. Pat. No. 2,630,437.

Furthermore, it has been found that (A) the compounds of the formula (Ia) and formula (Ib) wherein
$R^2$ represents $C_{1-10}$ alkyl which may be unsubstituted or substituted with halogen, or represents $C_{2-4}$ alkoxyalkyl, $C_{2-4}$ hydroxyalkyl or $C_{3-6}$ cycloalkyl, and
$R^2$ represents hydrogen can be obtained when compounds of the formula (II)

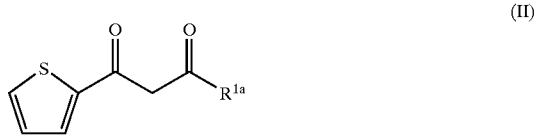

wherein
$R^{1a}$ represents $C_{1-10}$ alkyl which may be unsubstituted or substituted with halogen, or represents $C_{2-4}$ alkoxyalkyl, $C_{2-4}$ hydroxyalkyl or $C_{3-6}$ cycloalkyl,
are reacted with hydrazine hydrate, if appropriate, in the presence of one or more inert diluents, (B) the compounds of the formula (Ia) and the formula (Ib) wherein
$R^2$ represents $C_{1-9}$ alkoxy which may be unsubstituted or substituted with halogen, $C_{3-6}$ cycloalkoxy, $C_{2-4}$ alkoxyalkoxy or $C_{2-3}$ alkynyloxy, and
$R^2$ represents hydrogen
can be obtained when
5-hydroxy-3-(2-thienyl)pyrazole of the formula (III)

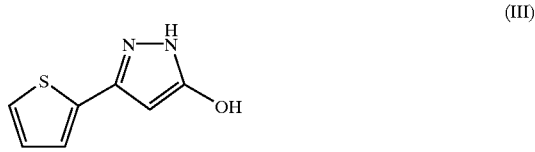

is reacted with compounds of the formula (IV)

wherein
$R^{1b}$ represents $C_{1-9}$ alkyl which may be unsubstituted or substituted with halogen, $C_{3-6}$ cycloalkyl, $C_{2-4}$ alkoxyalkyl or $C_{2-3}$ alkynyloxy, and
M represents halogen, methanesulfonyloxy, p-toluenesulfonyloxy or trifluoromethanesulfonyloxy,
in the presence of one or more inert diluent, and if appropriate, in the presence of an acid binder, (C) the compounds of the formula (Ia) and formula (Ib) wherein
$R^2$ represents $C_{1-4}$ alkoxycarbonyl, $C_{1-3}$ alkylcarbonyl or $C_{2-4}$ alkoxyalky can be obtained when compounds of the formula (Ic)

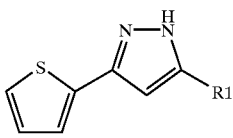

(Ic)

wherein
R¹ has the same definition as aforementioned,
are reacted with compounds of the formula (V)

R²ᵃ—Hal   (V)

wherein
R²ᵃ represents $C_{1-4}$ alkoxycarbonyl, $C_{1-3}$ alkylcarbonyl or $C_{2-4}$ alkoxyalkyl, and
Hal represents halogen,
in the presence of one or more inert diluents, and if appropriate, in the presence of an acid binder.

Finally, it has been found that the compounds of the formula (Ia) and formula (Ib) of the present invention have pronounced biological properties and are suitable especially for controlling animal pests. They especially show strong nematicidal activity and show good compatibility with crops. Therefore, the thienyl-pyrazoles of the formula (Ia) and formula (Ib) of the present invention are very useful as an effective agent for controlling animals pests.

In the present specification "Halogen" represents fluoro, chloro, bromo or iodo.

"Alkyl" may be straight chain or branched chain and there may be mentioned, for example, methyl, ethyl, propyl, isopropyl, n-, iso-, sec- or tert-butyl, n-, iso-, neo- or tert-pentyl, n- or iso-hexyl, heptyl, octyl, nonyl, decyl etc.

"Cycloalkyl" includes, for example, cyclopropyl, cyclobutyl, cyclopentyl, cyclohexyl etc.

"Alkoxy" may be straight chain or branched chain and there may be mentioned, for example, ethoxy, propoxy, iso-propoxy, n-, iso-, sec- or tert-butoxy, pentyloxy, hexyloxy etc.

"Alkoxyalkyl" is an alkoxy-substituted alkyl and there may be mentioned, for example, methoxymethyl, ethoxymethyl, propoxymethyl, isopropoxymethyl, n-, iso-, sec- or tert-butoxymethyl, n-, iso-, sec-, tert- or neo-pentoxymethyl etc.

"Alkoxyalkoxy" is an alkoxy-substituted alkoxy and there may be mentioned, for example, methoxymethoxy, ethoxymethoxy etc.

"Cycloalkoxy" includes, for example, cyclopropoxy, cyclobutyloxy, cyclopentyloxy, cyclohexyloxy etc.

"Alkynyloxy" includes, for example, propargyloxy etc.

As "alkoxycarbonyl" there may be mentioned, for example, methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl etc.

As "alkylcarbonyl" there may be mentioned, for example, acetyl, ethylcarbonyl etc.

Preferred substituents or ranges of the radicals listed in the formulae (Ia) and (Ib) mentioned hereinabove and hereinbelow are illustrated below.

R¹ preferably represents $C_{2-6}$ alkyl which may be unsubstituted or substituted with fluoro or chloro, or represents methoxymethyl, $C_{3-4}$ hydroxyalkyl, cyclopropyl, cyclopentyl, cyclohexyl, hydroxy, $C_{2-5}$ alkoxy which may be unsubstituted or substituted with fluoro or chloro, or represents cyclopentyloxy, cyclohexyloxy or $C_{2-3}$ alkoxyalkoxy.

R² preferably represents hydrogen, tert-butoxycarbonyl, $C_{1-2}$ alkylcarbonyl or $C_{2-3}$ alkoxyalkyl.

R¹ particularly preferably represents $C_{2-6}$ alkyl which may be unsubstituted or substituted with fluoro or chloro, or represents methoxymethyl, $C_{3-4}$ hydroxyalkyl, cyclopropyl, cyclopentyl, cyclohexyl, $C_{3-4}$ alkoxy which may be unsubstituted or substituted with fluoro or chloro, or represents cyclopentyloxy, cyclohexyloxy or methoxymethoxy.

R² particularly preferably represents hydrogen or acetyl.

R¹ very particularly preferably represents n-butyl, n-pentyl, n-hexyl, trifluoromethyl, ethoxy or methoxy.

R² very particularly preferably represents hydrogen, acetyl, methoxycarbonyl, t-butoxycarbonyl, ethoxymethyl or methoxymethyl.

R¹ most particularly preferably represents n-butyl or n-pentyl.

R² most particularly preferably represents hydrogen.

In the following the preparation processes of the compounds of the formula (Ia) and the formula (Ib) of the present invention will be described in more detail.

As the formula (Ia) and formula (Ib) are in relation as isomers as aforementioned, the final products described in the present specification will be shown in either of the formulae (Ia) and (Ib) for the sake of convenience, unless specified otherwise. It should be understood, however, that the compound can be described according to formula (Ia) or according to formula (Ib), because the compound can exist as the one or the other isomer.

In the aforementioned process (A), 1-(2-thienyl)-1,3-nonanedione and hydrazine hydrate are, for example, used as starting materials. In this case process (A) can be represented by the following reaction scheme:

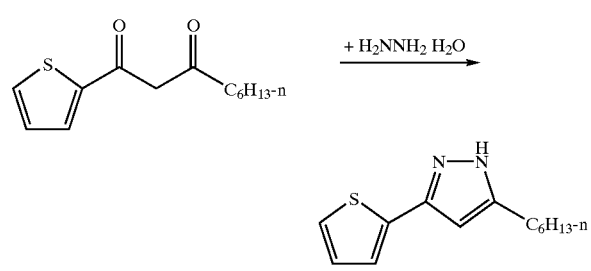

In the aforementioned process (B), 5-hydroxy-3-(2-thienyl)pyrazole and n-propyl bromide can, for example, be used as starting materials. In this case the preparation process (B) can be represented by the following reaction scheme:

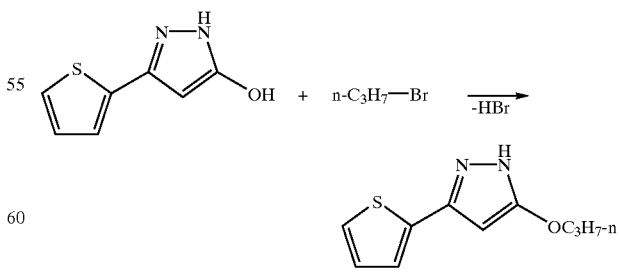

In the aforementioned process (C), 3-(2-thienyl)-5-(2,2,2 trifluoroethoxy)pyrazole and acetyl chloride can, for example, be used as starting materials. In this case process (C) can be represented by the following reaction scheme:

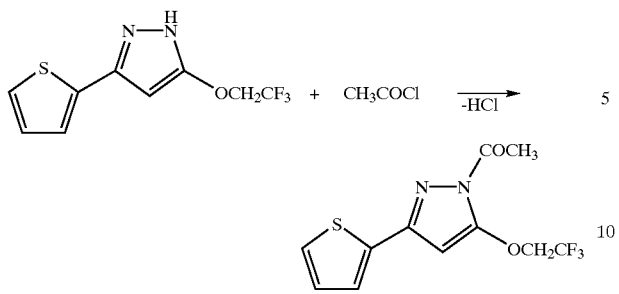

The compounds of the formula (II) used as starting material in the above-mentioned process (A) are the compounds based upon the aforementioned definition for compounds of the formula (II). As preferable compounds of the formula (II) there can be mentioned those compounds of the formula (II) wherein $R^{1a}$ corresponds to the preferred substituents or ranges of $R^1$ of the compounds of the formula (Ia) and the formula (Ib).

The compounds of the formula (II) are mostly known [cf., for example, Russ. J. Coord. Chem., 1998, Vol. 24, No. 9, pp.669–673, Japanese Laid-open Patent Publication No. 12617/1996, French Patent No. 2699919 Specification, Tetrahedron 1970, Vol. 26, No. 20, pp.4691–4696, J. Prakt. Chem., 1973, Vol. 315, No. 1, pp. 31–38, U.S. Pat. No. 3,700,416 etc.

The compounds of the formula (II) generally can be obtained by (D) reacting compounds of the formula (VI)

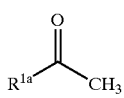

(VI)

wherein
$R^{1a}$ has the same definition as aforementioned,
with methyl 2-thiophenecarboxylate, or (E) by reacting compounds of the formula (VII)

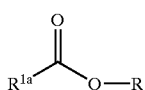

(VII)

wherein
$R^{1a}$ has the same definition as aforementioned, and
R represents methyl or ethyl,
with methyl 2-thienyl ketone.

The ketones of the formula (VI), methyl 2-thiophenecarboxylate, carboxylic acid esters of the formula (VII) and methyl 2-thienyl ketone are either compounds which can be purchased or can be easily obtained according to processes known to a person skilled in the art.

As specific examples of the compounds of the formula (VI) there may be mentioned n-butyl methyl ketone, methyl n-pentyl ketone, cyclopropyl methyl ketone, cyclopentyl methyl ketone, isopropyl methyl ketone and so on.

As specific examples of the compounds of the formula (VII) there may be mentioned methyl valerate, methyl hexanoate, methyl cyclopropanecarboxylate, methyl cyclopentanecarboxylate and so on.

The above-mentioned processes (D) and (E) can be conducted, for example, according to the method described in Organic Syntheses Collective, Vol. 111, p. 251.

As specific examples of the compounds of the aforementioned formula (II) there may be mentioned, for example,
1-(2-thienyl)-1,3-butanedione,
1-(2-thienyl)-1,3-pentanedione,
1-(2-thienyl)-1,3-hexanedione,
1-(2-thienyl)-1,3-heptanedione,
1-(2-thienyl)-1,3-octanedione,
1-(2-thienyl)-1,3-nonanedione,
1-(2-thienyl)-1,3-(5-fluoro)pentanedione,
1-(2-thienyl)-1,3-(6-fluoro)hexanedione,
1-(2-thienyl)-1,3-(6-trifluoromethyl)hexanedione,
1-(2-thienyl)-1,3-(7-fluoro)heptanedione,
1-(2-thienyl)-1,3-(7-chloro)heptanedione,
1-(2-thienyl)-1,3-(8-fluoro)octanedione,
1-(2-thienyl)-1,3-(3-cyclopropyl)propanedione,
1-(2-thienyl)-1,3-(4-methoxy)butanedione,
1-(2-thienyl)-1,3-(3-cyclopentyl)propanedione and so on.

5-Hydroxy-3-(2-thienyl)pyrazole, a starting material in process (B), is a known compound and is described, for example, in U.S. Pat. No. 2,630,437.

The compounds of the formula (IV), another starting material in the process (B), are well known compounds in the field of organic chemistry. As specific examples of the compounds of the formula (IV) there may be mentioned methyl iodide, ethyl iodide, n-propyl bromide, isopropyl iodide, n-butyl bromide, isobutyl bromide, n-pentyl bromide, sec-butyl bromide, n-hexyl bromide, cyclopentyl bromide, cyclohexyl bromide, methoxymethyl chloride, ethoxymethyl chloride, 1-(p-toluenesulfonyloxy)-2,2,2-(trifluoro)ethane and so on.

The compounds of the formula (Ic) used as a starting material in the process (C) correspond to the compounds of the formula (Ia) or the formula (Ib) wherein $R^2$ is hydrogen.

The compounds of the formula (V), another starting material in the process (C) are well known compounds in the field of organic chemistry. As specific examples there may be mentioned acetyl chloride, methoxymethyl chloride, tert-butyloxycarbonyl chloride and so on.

In case of preparing the compounds of the formula (Ia) and formula (Ib), wherein $R^2$ is a tert-butoxycarbonyl group, in the preparation process (C), di-tert-butyl dicarbonate can be used instead of the compound of the formula (V), wherein $R^{2a}$ represents tert-butoxycarbonyl.

The process (A) may be conducted in an adequate diluent. As examples of a diluent to be used in that case there can be mentioned all inert diluents, for example, water; aliphatic, alicyclic and aromatic hydrocarbons (which may optionally be chlorinated), for example pentane, hexane, cyclohexane, petroleum ether, ligroine, benzene, toluene, xylene, dichloromethane, chloroform, carbon tetetrachloride, 1,2-dichloroethane, chlorobenzene, dichlorobenzene etc.; ethers, for example diethyl ether, methyl ethyl ether, diisopropyl ether, dibutyl ether, dioxane, dimethoxyethane (DME), tetrahydrofuran (THF), diethylene glycol dimethyl ether (DGM) etc.; nitriles, for example acetonitrile, propionitrile, acrylonitrile etc.; alcohols, for example methanol, ethanol, isopropanol, butanol, ethylene glycol etc.; acid amides, for example dimethylformamide (DMF), dimethylacetamide (DMA), N-methylpyrrolidone, 1,3-dimethyl-2-imidazolidinone, hexamethylphosphoric triamide (HMPA) and so on.

The process (A) can be conducted in a substantially wide range of temperature. In general, the reaction is carried out between −20 and 150° C., preferably between 20 and 120°

C. Although said reaction is conducted desirably under normal (atmospheric) pressure, it can be conducted optionally under elevated pressure or under reduced pressure.

The molar ratio of the compounds of formula (II) to hydrazine hydrate is generally 1:5 to 5:1.

For example, by reacting 1–5 moles of hydrazine hydrate with 1 mole of the compounds of the formula (II) in a diluent, for example, ethanol, the compounds of the corresponding formulae (Ia) and (Ib) can be obtained.

Process (B) may be conducted in an adequate diluent. As examples of the diluents used in that case there can be mentioned all inert diluents, for example water; aliphatic, alicyclic and aromatic hydrocarbons (which may optionally be chlorinated), for example, hexane, cyclohexane, petroleum ether, ligroine, benzene, toluene, xylene, dichloromethane, chloroform, carbon tetrachloride, 1,2-dichloroethane, chlorobenzene etc.; ethers, for example diethyl ether, methyl ethyl ether, diisopropyl ether, dibutyl ether, propylene oxide, dioxane, dimethoxyethane (DME), tetrahydrofuran (THF), diethylene glycol dimethyl ether (DGM) etc.; ketones, for example acetone methyl ethyl ketone, methyl isopropyl ketone, methyl isobutyl ketone etc.; nitriles, for example acetonitrile, propionitrile, acrylonitrile etc.; esters, for example ethyl acetate, amyl acetate etc.; acid amides, for example dimethylformamide (DMF), dimethylacetamide (DMA), N-methylpyrrolidone, 1,3-dimethyl-2-imidazolidinone, hexamethylphosphoric triamide (HMPA) etc.; sulfones and sulfoxides, for example dimethyl sulfoxide (DMSO), sulfolane and so on.

Process (B) may be conducted in the presence of an acid binder. As acid binders which can be used in this case there can be mentioned, for example, hydroxides, carbonates, bicarbonates and alcoholates etc. of alkali metals; tertiary amines, dialkylaminoanilines and pyridines, for example triethylamine, diethylaniline, pyridine, 4-dimethylaminopyridine, 1,4-diazabicyclo[2,2,2]octane (DABCO), 1,8-diazabicyclo[5,4,0]undec-7-ene (DBU) and so on.

Process (B) may also be conducted with the help of phase-transfer catalysts. As examples of diluents usable in this case there can be mentioned water; aliphatic, alicyclic and aromatic hydrocarbons (which may optionally be chlorinated), for example pentane, hexane, cyclohexane, petroleum ether, ligroine, benzene, toluene, xylene, dichloromethane, chlorobenzene, dichlorobenzene etc.; ethers, for example diethyl ether, methyl ethyl ether, diisopropyl ether, dibutyl ether, dioxane, dimethoxyethane (DME), tetrahydrofuran (THF), diethylene glycol dimethyl ether (DGM) and so on.

As examples of phase-transfer catalysts there can be mentioned quaternary ions, for example tetramethylammonium bromide, tetrapropylammonium bromide, tetrabutylammonium bromide, tetrabutylammonium hydrogen sulfate, tetrabutylammonium iodide, trioctylmethylammonium chloride, benzyltriethylammonium bromide, butylpyridinium bromide, heptylpyridinium bromide, benzyltriethylammonium chloride etc.; crown ethers, for example, dibenzo-18-crown-6, dicyclohexyl-18-crown-6, 18-crown-6 etc.; cryptands, for example [2.2.2]-cryptate, [2.1.1]-cryptate, [2.2.1]cryptate, [2.2.B]-cryptate, [3.2.2]-cryptate and so on.

Process (B) may be conducted in a substantially wide range of temperature. In general, the reaction is carried out between 0 and 200° C., preferably between 0 and 120° C. Although said reaction is conducted desirably under normal (atmospheric) pressure, it may be conducted optionally under elevated pressure or under reduced pressure.

The molar ratio of the compound of formula (IV) to the compound of formula (III) is generally 3:1 to 1:3, preferably 1.5:1 to 1:1.5.

For example by reacting 1–1.5 moles of the compound of the formula (IV) with I mole of the compound of the formula (III) in a diluent, for example acetonitrile in the presence of, for example, potassium carbonate and 18-crown6-ether, the compounds of the corresponding formulae (Ia) and (Ib) can be obtained.

Process (C) may be conducted in an adequate diluent. As a diluent which can be used in this case there can be mentioned all inert diluents, for example aliphatic, alicyclic and aromatic hydrocarbons (which may optionally be chlorinated), for example pentane, hexane, cyclohexane, petroleum ether, ligroine, benzene, toluene, xylene, dichloromethane, chloroform, carbon tetetrachloride, chlorobenzene, dichlorobenzene etc.; ethers, for example diethyl ether, methyl ethyl ether, diisopropyl ether, dibutyl ether, dioxane, dimethoxyethane (DME), tetrahydrofuran (THF), diethylene glycol dimethyl ether (DGM) etc.; nitriles, for example acetonitrile, propionitrile, acrylonitrile etc.; alcohols, for example, methanol, ethanol, isopropanol, butanol, ethylene glycol etc.; esters, for example ethyl acetate, amyl acetate etc.; acid amides, for example dimethylformamide (DMF), dimethylacetamide (DMA), N-methylpyrrolidone, 1,3-dimethyl-2-imidazolidinone, hexamethylphosphoric triamide (HMPA) etc.; sulfones and sulfoxides, for example dimethyl sulfoxide (DMSO), sulfolane and so on.

The reaction of Process (C) may be conducted in the presence of an acid binder. As acid binders which can be used in this case the same compounds as mentioned in the aforementioned process (B) can be exemplified.

Process (C) may be conducted in a substantially wide range of temperature. In general, the reaction is carried out between −50 and 150° C., preferably between −20 and 100° C. Although said reaction is conducted desirably under normal (atmospheric) pressure, it may be conducted optionally also under elevated pressure or under reduced pressure.

The molar ratio of the compound of formula (V) to the compound of formula (Ic) is generally 5:1 to 1:5, preferably 3:1 to 1:3. For example, by reacting 1–5 moles of the compound of the formula (V) with 1 mole of the compounds of the formula (Ic) in a diluent, for example, tetrahydrofuran in the presence of potassium carbonate, the compounds of the corresponding formulae (Ia) and (Ib) can be obtained.

As another process for preparing the compounds of the formulae (Ia) and (Ib) in case $R^2$ is $C_{1-4}$ alkoxycarbonyl, as shown in an example later, there. can be mentioned a process which makes use of di-($C_{1-4}$ alkyl) dicarbonate instead of the compounds corresponding to the formula (V) to react with the compounds of the formula (Ic) in the above-mentioned process (C).

The compounds of the formula (Ia) and formula (Ib) of the present invention show strong activity against harmful organisms, particularly against nematodes. The compounds of the present invention can, therefore, be used as nematicidal agents. It is remarkable, that the active compounds of the present invention do not exhibit phytotoxic activity against crops and exhibit remarkable controlling-effects towards harmful nematodes.

The phytoparasitic nematodes include, for example, Pratylenchus spp., *Radopholus similis, Ditylenchus dipsaci, Tylenchulus semipenetrans*, Heterodera spp., Globodera spp., Meliodogyne spp., Aphelenchoides spp., Longidorus spp., Xiphinema spp., Trichodorus spp., and Bursaphelenchus spp., The compounds of the present invention are especially useful against, for example, Pratylenchus spp., *Globodera rostochiensis* Wollenweber, *Heterodera glycines* Ichinohe, Meloidogyne spp., *Aphelenchoides basseyi* Christie, Bursaphelenchus Xylophilus etc. However, the application of the compounds according to the present invention is not limited to them.

The active compounds according to the invention, as such or in their formulations, can also be used in a mixture with known fungicides, bactericides, acaricides, nematicides or insecticides, to widen, for example, the activity spectrum or to prevent the development of resistance. In many cases, this results in synergistic effects, i.e. the activity of the mixture exceeds the activity of the individual components.

Examples of particularly advantageous mixing components are the following:

Fungicides:
- aldimorph, ampropylfos, ampropylfos potassium, andoprim, anilazine, azaconazole, azoxystrobin,
- benalaxyl, benodanil, benomyl, benzamacril, benzamacril-isobutyl, bialaphos, binapacryl, biphenyl, bitertanol, blasticidin-S, bromuconazole, bupirimate, buthiobate,
- calcium polysulphide, capsimycin, captafol, captan, carbendazim, carboxin, carvon, quinomcthionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
- ediphenphos, epoxiconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
- guazatine,
- hexachlorobenzene, hexaconazole, hymexazole,
- imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
- kasugamycin, kresoxim-methyl, copper preparations, such as: copper hydroxide, copper naphthenate, copper oxychloride, copper sulphate, copper oxide, oxine-copper and Bordeaux mixture,
- mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene (PCNB),
- sulphur and sulphur preparations,
- tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
- uniconazole,
- validamycin A, vinclozolin, viniconazole,
- zarilamide, zineb, ziram and also
- Dagger G,
- OK-8705,
- OK-8801,
- α-(1,1-dimethylethyl)-β-(2-phenoxyethyl)-1H-1,2,4-triazole-1-ethanol,
- α-(2,4-dichlorophenyl)-β-fluoro-b-propyl-1H-1,2,4-triazole-1-ethanol,
- α-(2,4-dichlorophenyl)-β-methoxy-a-methyl-1H-1,2,4-triazole-1-ethanol,
- α-(5-methyl-1,3-dioxan-5-yl)-β-[[4-(trifluoromethyl)-phenyl]-methylene]-1H-1,2,4-triazole-1-ethanol,
- (5RS,6RS)-6-hydroxy-2,2,7,7-tetramethyl-5-(1H-1,2,4-triazol-1-yl)-3-octanone,
- (E)-a-(methoxyimino)-N-methyl-2-phenoxy-phenylacetamide,
- isopropyl 1-{2-methyl-1-[[[1-(4-methylphenyl)-ethyl]-amino]-carbonyl]-propyl}-carbamate,
- 1-(2,4-dichlorophenyl)-2-(1H-1,2,4-triazol-1-yl)-ethanone O-(phenylmethyl) oxime,
- 1-(2-methyl-1-naphthalenyl)-1H-pyrrol-2,5-dione,
- 1-(3,5-dichlorophenyl)-3-(2-propenyl)-2,5-pyrrolidinedione,
- 1-[(diiodomethyl)-sulphonyl]-4-methyl-benzene,
- 1-[[2-(2,4-dichlorophenyl)-1,3-dioxolan-2-yl]-methyl]-1H-imidazole,
- 1-[[2-(4-chlorophenyl)-3-phenyloxiranyl]-methyl]-1H-1,2,4-triazole,
- 1-[1-[2-[(2,4-dichlorophenyl)-methoxy]-phenyl]-ethenyl]-1H-imidazole,
- 1-methyl-5-nonyl-2-(phenylmethyl)-3-pyrrolidinole,
- 2',6'-dibromo-2-methyl-4'-trifluoromethoxy-4'-trifluoro-methyl-1,3-thiazole-5-carboxanilide,
- 2,2-dichloro-N-[1-(4-chlorophenyl)-ethyl]-1-ethyl-3-methyl-cyclopropanecarboxamide,
- 2,6-dichloro-5-(methylthio)-4-pyrimidinyl thiocyanate,
- 2,6-dichloro-N-(4-trifluoromethylbenzyl)-benzamide,
- 2,6-dichloro-N-[[4-(trifluoromethyl)-phenyl]-methyl]-benzamide,
- 2-(2,3,3-triiodo-2-propenyl)-2H-tetrazole,
- 2-[(1-methylethyl)-sulphonyl]-5-(trichloromethyl)-1,3,4-thiadiazole,
- 2-[[6-deoxy-4-O-(4-O-methyl-β-D-glycopyranosyl)-a-D-glucopyranosyl]-amino]-4methoxy-1H-pyrrolo[2,3-d]pyrimidine-5-carbonitrile,
- 2-aminobutane,
- 2-bromo-2-(bromomethyl)-pentanedinitrile,
- 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrol-2,5-dione,
3,5-dichloro-N-[cyano-[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate, and
spiro[2H]-1-benzopyran-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricide/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopernethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoat, oxamyl, oxydemethon M,
*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*,

YI 5302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate.

4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-puridazinone, 4-chloro-2-(2-chloro-2-methylpropyl)-5-[(6-iodo-3-pyridinyl)methoxy]-3(2H)pyridazin 4-chloro-5-[(6-chloro-3-pyridinyl)methoxy]-2-(3,4-dichlorophenyl)-3(2H)pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoroamidothioate.

A mixture with other known active compounds, such as herbicides, or with fertilizers and growth regulators is also possible.

Furthermore, when used as insecticides, the active compounds according to the invention can be present in their commercial formulations and in the use forms, prepared from these formulations, as a mixture with synergists. Synergists are compounds which increase the action of the active compounds, without it being necessary for the synergist added to be active itself.

The active-compound content of the use forms prepared from the conmmercial formulations can vary within wide limits. The active-compound concentration of the use forms can be from 0.0000001 to 100% by weight of active compound, preferably between 0.0001 and 1% by weight. Application is carried out in a customary manner adapted to the use forms.

The active compounds of the present invention can be converted into the customary formulations, such as solutions, emulsions, wettable powders, water dispersible granules, suspensions, powders, soluble powders, foaming agents, pastes, dusting agents, suspo-emulsion concentrates, granules, active compound-impregnated natural and synthetic substances, microcapsules, fumigants etc.

These formulations can be prepared according to per se known methods, for example, by mixing the active compounds with extenders, namely liquid carriers, liquefied gas or solid diluents or carriers, and optionally with surface-active agents, namely emulsifiers and/or dispersants and/or foam-forming agents. When water is used as extender, for example, organic solvents can be used as auxiliary solvents.

As liquid diluents or carriers there can be mentioned, for example, aromatic hydrocarbons, for example xylene, toluene, alkylnaphthalene etc., chlorinated aromatic or chlorinated aliphatic hydrocarbons, for example chlorobenzenes, ethylene chlorides, methylene chloride etc., aliphatic hydrocarbons, for example, cyclohexane etc. or paraffins such as mineral oil fractions etc., alcohols, for example butanol, glycols and their ethers and esters etc., ketones, for example acetone, methyl ethyl ketone, methyl isobutyl ketone, cyclohexanone etc., strongly polar solvents, for example dimethylformamide, dimethyl sulphoxide etc., water etc. If the extender used is water, it is also possible to use, for example, organic solvents as auxiliary solvents.

Liquefied gas diluents or carriers are liquefied substances which are gases at normal temperature and pressure, for example aerosol propellants such as butane, propane, nitrogen gas, carbon dioxide, halogenated hydrocarbons, etc.

As solid diluents there can be mentioned, for example, ground natural minerals, such as kaolin, clay, talc, chalk, quartz, attapulgite, montmorillonite, diatomaceous earth etc., ground synthetic minerals, such as highly dispersed silicic acid, alumina, silicates etc.

As solid carriers for granules there can be mentioned, for example, crushed and fractionated rocks, such as calcite, marble, pumice, sepiolite, dolomite etc., synthetic granules of inorganic and organic meals, particles of organic materials, such as sawdust, coconut shells, maize cobs, tobacco stalks, etc.

As emulsifiers and/or foam-forming agents there can be mentioned, for example, nonionic and anionic emulsifiers, such as plyoxyethylene fatty acid esters, polyoxyethylene fatty acid alcohol ethers, for example alkylaryl polyglycol ethers, alkylsulphonates, alkylsulphates, arylsulphonates etc., albumin hydrolysis products etc.

Dispersants may be, for example, ligninsulphite waste liquor, methyl cellulose etc.

Tackifiers may also be used in formulations like powders, granules or emulsions. Tackifiers can be, for example, carboxymethyl cellulose, natural and synthetic polymers, such as gum arabic, polyvinyl alcohol, polyvinyl acetate etc.

It is possible to use colorants such as inorganic pigments, for example iron oxide, titanium oxide, Prussian Blue or organic dyestuffs such as alizarin dyestuffs, azo dyestuffs or metal phthalocyanine dyestuffs, and trace nutrients such as salts of metals like iron, manganese, boron, copper, cobalt, molybdenum, zinc etc.

The formulations in general contain between 0.01 and 95 per cent by weight of active compound, preferably between 0.5 and 90%.

The preparation and application of the compounds of the present invention will be described more specifically by the following examples. However, the present invention should not be restricted to them in any way. "Parts" mean "parts by weight" unless specified otherwise.

PREPARATION EXAMPLES

Example 1

Process (A)

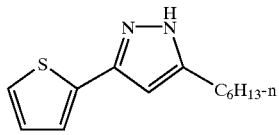

In ethanol (20 ml), 1-(2-thienyl)-1,3-nonanedione (1.30 g) and hydrazine hydrate (1.26 g) are refluxed for 3 hours by heating. After the reaction is completed, the solvent is distilled off. The obtained residue is added to petroleum ether and crystallized to obtain the objective 3-(2-thienyl)-5-n-hexylpyrazole (0.76 g) as colorless crystals. mp. 53–55° C.

Example 2

Process (B)

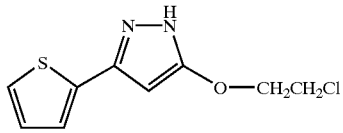

5-Hydroxy-3-(2-thienyl)pyrazole (2.49 g), potassium carbonate (3.11 g) and 18-crown-6-ether (0.13 g) is suspended in acetonitrile (31 ml), to which 1-bromo-2-chloroethane (2.15 g) is added drop by drop and the reaction mixture is refluxed for 5 hours by heating. After the reaction is completed, it is extracted with ethyl acetate, washed with aqueous solution of sodium hydrogen carbonate and dried with anhydrous magnesium sulfate. Dichloromethane is added to the residue obtained by distilling off ethyl acetate and the insoluble matter is filtered off. Dichloromethane is added and distilled off to obtain the objective 5-(2-chloroethoxy)-3-(2-thienyl)pyrazole (1.0 g). mp. 134–138° C.

Example 3

Process (C)

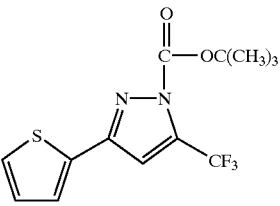

5-Trifluoromethyl-3-(2-thienyl)pyrazole (1.50 g) is dissolved in acetonitrile (30 ml), to which di-tert-butyl dicarbonate (2.25 g) is added under cooling with ice. Then 4-dimethylaminopyridine (0.42 g) is added and the reaction mixture is stirred for 3 hours at room temperature. After the reaction is completed, the solvent is distilled off and the residue is purified by silica gel column chromatography (eluent hexane:ethyl acetate=10:1) to obtain the objective 1-tert-butoxycarbonyl-5-trifluoromethyl3-(2-thienyl)pyrazole (1.6 g).

$n_D^{20}=1.5168$

The compounds of the formula (Ia) and formula (Ib) of the present invention obtained by processes corresponding to the above-mentioned Preparation Examples 1 and 2 are shown in Table 1, together with the compounds of Examples 1 and 2. Further, in Table 2, known compounds having harmful pesticidal activity are shown.

TABLE 1

(Ia)

(Ib)

| Compound No. | $R^1$ | $R^2$ | mp. °C./$n_D^{20}$ |
|---|---|---|---|
| 1 | $CH_2CH_3$ | H | 103–107 |
| 2 | $CH_2CH_2CH_3$ | H | 96–102 |
| 3 | $CH(CH_3)_2$ | H | 102–109 |
| 4 | $CH_2CH(CH_3)_2$ | H | NMR(DMSO-$d_6$) 0.83(6H, d) 1.83(1H, m) 2.42(2H, d) 6.30(1H, s) 6.83–7.40 (3H, m) 12.23(1H, m) |
| 5 | $CH(CH_3)CH_2CH_3$ | H | |
| 6 | $C(CH_3)_3$ | H | 129–130 |
| 7 | $CH(CH_3)CH_2CH_2CH_3$ | H | 1.5585 |
| 8 | $CH(CH_3)CH(CH_3)_2$ | H | |
| 9 | $CH(C_2H_5)_2$ | H | 112–114 |
| 10 | $CH_2CH_2CH(CH_3)_2$ | H | 1.5748 |
| 11 | $CH_2CH(CH_3)CH_2CH_3$ | H | |

TABLE 1-continued

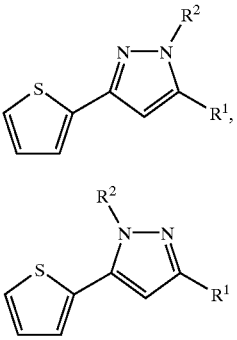
(Ia)

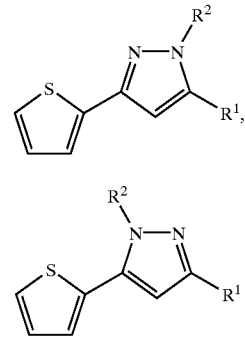
(Ib)

| Compound No. | R¹ | R² | mp. °C./$n_D^{20}$ |
|---|---|---|---|
| 12 | $C(CH_3)_2CH_2CH_3$ | H | |
| 13 | $CH_2C(CH_3)_3$ | H | 1.5885 |
| 14 | $C_6H_{13}$-n | H | 53–55 |
| 15 | $CH(CH_3)CH_2(CH_2)_2CH_3$ | H | |
| 16 | $CH_2CH(CH_3)CH_2CH_2CH_3$ | H | |
| 17 | $CH_2CH_2CH(CH_3)CH_2CH_3$ | H | |
| 18 | $CH_2(CH_2)_2CH(CH_3)_2$ | H | |
| 19 | $C_7H_{15}$-n | H | 85–87 |
| 20 | $CH(C_2H_5)CH_2(CH_2)_2CH_3$ | H | 95–97 |
| 21 | $C_8H_{17}$-n | H | 82–83 |
| 22 | $C_9H_{19}$-n | H | 87–89 |
| 23 | $C_{10}H_{21}$-n | H | 79–84 |
| 24 | $CF_3$ | H | 121–126 |
| 25 | $CH_2CH_2F$ | H | |
| 26 | $CH_2CH_2Cl$ | H | |
| 27 | $CH_2CF_3$ | H | |
| 28 | $CF_2CF_3$ | H | |
| 29 | $CH_2CH_2CH_2F$ | H | |
| 30 | $CH_2(CH_2)_2Cl$ | H | 1.4619 |
| 31 | $CF_2CF_2CF_3$ | H | |
| 32 | $CH_2(CH_2)_3F$ | H | |
| 33 | $CH_2(CH_2)_3Cl$ | H | |
| 34 | $CH_2(CH_2)_4F$ | H | |
| 35 | $CH_2(CH_2)_4Cl$ | H | |
| 36 | $CH_2OCH_3$ | H | 1.609 |
| 37 | $CH_2(CH_2)_2OH$ | H | |
| 38 | $CH_2(CH_2)_3OH$ | H | |
| 39 |  | H | 88–90 |
| 40 | 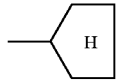 | H | 115–119 |
| 41 | 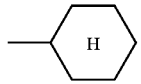 | H | 155–159 |
| 42 | $OCH_3$ | H | 1.5865 Mixture of position isomers (about 1:1) |
| 43 | $OCH_2CH_3$ | H | 85–86 |
| 44 | $O(CH_2)_2CH_3$ | H | 118–119 |
| 45 | $OCH_2CF_2CHF_2$ | H | 105–107 |
| 46 | $OCH(CH_3)_2$ | H | |
| 47 | $OC_4H_9$-n | H | 1.424 |
| 48 | $OCH_2CH(CH_3)_2$ | H | 100–103 |
| 49 | $OCH(CH_3)CH_2CH_3$ | H | 1.5765 |
| 50 | $OC_5H_{11}$-n | H | 83–87 |
| 51 | $OCH(CH_3)CH_2CH_2CH_3$ | H | 1.5680 |
| 52 | $OCH(CH_3)CH(CH_3)_2$ | H | |
| 53 | $OCH(C_2H_5)_2$ | H | 1.5643 |

TABLE 1-continued

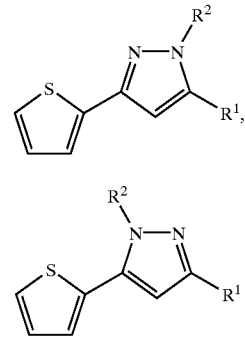
(Ia)

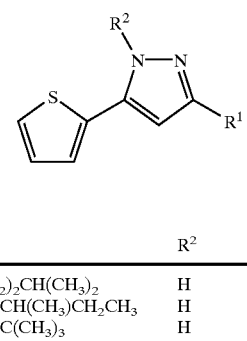
(Ib)

| Compound No. | R¹ | R² | mp. °C./$n_D^{20}$ |
|---|---|---|---|
| 54 | $O(CH_2)_2CH(CH_3)_2$ | H | 179–181 |
| 55 | $OCH_2CH(CH_3)CH_2CH_3$ | H | 1.5695 |
| 56 | $OCH_2C(CH_3)_3$ | H | 116–118 |
| 57 | $OC_6H_{13}$-n | H | 79–80 |
| 58 | $OC_7H_{15}$-n | H | 89–92 |
| 59 | $OC_8H_{17}$-n | H | 94–95 |
| 60 | $OC_9H_{19}$-n | H | 67–73 |
| 61 |  | H | 99–103 |
| 62 | 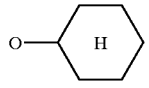 | H | |
| 63 | $OCHF_2$ | H | |
| 64 | $OCF_3$ | H | |
| 65 | $OCH_2CH_2F$ | H | 109–117 |
| 66 | $OCH_2CHF_2$ | H | 126–130 |
| 67 | $OCH_2CF_3$ | H | 108–114 |
| 68 | $OCH_2CH_2Cl$ | H | 134–138 |
| 69 | $O(CH_2)_2CH_2F$ | H | 103–105 |
| 70 | $O(CH_2)_2CH_2Cl$ | H | |
| 71 | $OCH_2CH(CH_3)CH_2Cl$ | H | 91–92 |
| 72 | $O(CH_2)_3CH_2F$ | H | |
| 73 | $O(CH_2)_3CH_2Cl$ | H | 1.6113 |
| 74 | $OCH_2OCH_3$ | H | 82–91 |
| 75 | $OCH_2OCH_2CH_3$ | H | 1.5782 |
| 76 | $OCH_2C\equiv CH$ | H | 102–110 |
| 77 | $CF_3$ | $CO_2C(CH_3)_3$ | 1.5168 |
| 78 | $OCH_2CF_3$ | $COCH_3$ | 61–68 |
| 79 | $OCH_2OCH_3$ | $CH_2OCH_3$ | 1.551 |
| 80 | $OCH_2OCH_2CH_3$ | $CH_2OCH_2CH_3$ | 1.5439 |

TABLE 2

| Compound No. | R¹ | R² | mp.° C. |
|---|---|---|---|
| 81 | $CH_3$ | H | 133–135 |
| 82 | $C_4H_9$-n | H | 47–48 |
| 83 | $C_5H_{11}$-n | H | 68–73 |
| 84 | OH | H | 144–146 |

USE EXAMPLES 1

Example A

Test Against Meloidogyne spp. (Soil Pot Test)

Preparation of Test Agent:

1 Part of the active compound is impregnated to 99 parts of pumice to obtain fine granules.

Test Method:

The active compound prepared as mentioned above is added to soil contaminated with Meloidogyne incognita to a final concentration of 50 ppm and then homogeneously mixed by stirring. Then a pot (1/5000 are) was filled with the soil. About 20 seeds of tomato (variety: Kurihara) were sown per pot. After cultivation in a greenhouse for 4 weeks, they were carefully pulled out not to damage the root and the root knot index and the controlling effect of the compound tested were determined as follows:

Degree of damage 0: No knot was formed (Complete control).
1: A few knots were formed.
2: Knots were formed to a medium extent.
3: Knots were formed to an intense extent.
4: Knots were formed to the most intense extent (which corresponds to non-treatment).

Based on the degree of damage acording to the aforementioned standard (0–4), the root knot index can be determined as follows (Equation 1)

$$\text{Root knot index} = \frac{\Sigma(\text{degree of damage} \times \text{number of individuals})}{\text{Total number of tested individuals} \times 4} \quad \text{Equation 1}$$

The controlling effect which can be achieved by applying compounds according to the present invention can then be determined as follows (Equation 2):

$$\text{Controlling effect} = \frac{\left(\begin{array}{c}\text{Root knot index at} \\ \text{non-treated area}\end{array} - \begin{array}{c}\text{Root knot index at} \\ \text{treated area}\end{array}\right)}{\text{Root knot index at non-treated area}} \times 100 \quad \text{Equation 2}$$

The evaluation of the controlling effect towards nematodes is then done by connecting the values of the controlling effect with the following standards (a–d):

a: Controlling effect 100–71%
b: Controlling effect 70–50%
c: Controlling effect less than 50%
d: Controlling effect 0%

The results are shown in the following Table 3 with representative examples.

TABLE 3

| Compound No. | Concentration of active ingredient | Evaluation of controlling effect |
|---|---|---|
| 43 | 50 | a |
| 44 | 50 | a |
| 45 | 50 | a |
| 47 | 50 | a |
| 48 | 50 | a |
| 49 | 50 | a |
| 82 | 50 | a |
| 83 | 50 | a |

FORMULATION EXAMPLES

Example I

Granule

To a mixture of 10 parts of the compound of Example 2, 30 parts of bentonite (montmorillonite), 58 parts of talc and 2 parts of ligninsulphonate salt, 25 parts water are added, well kneaded, formed into granules of 10–40 mesh with the help of an extrusion granulator and dried at a temperature of between 40–50° C. to obtain granules.

Example II

Granule

95 Parts of clay mineral particles having a particle diameter distribution of 0.2–2 mm are put into a rotary mixer. While rotating it, 5 parts of the compound of Example 4 are sprayed together with a liquid diluent, and the uniformly wetted particles are then dried at a temperature of between 40° C. and 50° C. to obtain granules.

Example 3

Emulsifiable Concentrates

30 Parts of the compound of Example 6, 55 parts of xylene, 8 parts of polyoxyethylene alkyl phenyl ether and 7 parts of calcium alkylbenzenesulphonate are mixed and stirred to obtain an emulsion.

Example 4

Wettable Powder

15 Parts of the compound of Example 14, 80 parts of a mixture of white carbon (hydrous amorphous silicon oxide fine powders) and powder clay (1:5), 2 parts of sodium alkylbenzenesulphonate and 3 parts of sodium alkylnaphthalenesulphonate-formalin-condensate are crushed and mixed to produce a wettable powder.

What is claimed is:

1. A compound selected from the group consisting of a compound of the formula (Ia) and a compound of the formula (Ib)

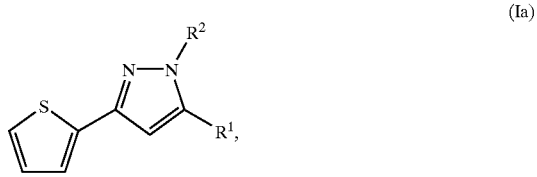

wherein
$R^1$ represents $C_{1-9}$ alkoxy which may be unsubstituted or substituted with halogen,
$R^2$ represents hydrogen.

2. The compound according to claim 1, wherein
$R^1$ represents $C_{2-5}$ alkoxy which may be unsubstituted or substituted with fluoro or chloro, and
$R^2$ represents hydrogen.

3. The compound according to claim 1 wherein
$R^1$ represents $C_{3-4}$ alkoxy which may be unsubstituted or substituted with fluoro or chloro, and
$R^2$ represents a hydrogen atom.

4. The compound according to claim 1 wherein $R^1$ represents ethoxy or methoxy, and $R^2$ represents hydrogen.

5. A process for preparing a compound selected from the group consisting of a compound of the formula (Ia) according to claim 1 and a compound of the formula (Ib) according to claim 1
wherein $R^1$ represents $C_{1-9}$ alkoxy which may be unsubstituted or substituted with halogen, and $R^2$ represents hydrogen comprising the step of:

reacting 5-hydroxy-3-(2-thienyl)pyrazole of the formula (III)

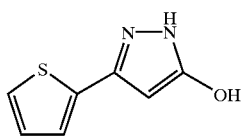

(III)

with a compound of the formula (IV)

$$R^{1b}\text{—M} \qquad (IV)$$

wherein $R^{1b}$ represents $C_{1-9}$ alkyl which may be unsubstituted or substituted with halogen, or represents $C_{3-6}$ cycloalkyl, $C_{2-4}$ alkoxyalkyl or $C_{2-3}$ alkynyloxy, and M represents halogen, methanesulfonyloxy, p-toluenesulfonyloxy or trifluoromethanesulfonyloxy, optionally in the presence of one or more inert diluents, and, optionally, in the presence of an acid binder.

6. A method for controlling pests, comprising the step of allowing a pesticidally effective amount of one or more compounds selected from the group consisting of one or more compounds of the formula (Ia) according to claim 2 and one or more compounds of the formula (Ib) according to claim 2 to act on a member selected from the group consisting of said pests, a locus from which it is desired to exclude such pests, and combinations thereof.

* * * * *